United States Patent [19]

Schreiber et al.

[11] 4,418,419
[45] Nov. 29, 1983

[54] DENTAL TOMOGRAPHY APPARATUS

[75] Inventors: Peter Schreiber, Rellingen; Eberhard Steenfadt, Stade, both of Fed. Rep. of Germany; Gerard P. M. Bergman, DJ Eindhoven, Netherlands

[73] Assignee: U.S. Philips Corporation, New York, N.Y.

[21] Appl. No.: 416,792

[22] Filed: Sep. 10, 1982

Related U.S. Application Data

[63] Continuation of Ser. No. 238,350, Feb. 26, 1981, abandoned.

[30] Foreign Application Priority Data

Mar. 1, 1980 [DE] Fed. Rep. of Germany ....... 3007935

[51] Int. Cl.³ ............................................... A61B 6/14
[52] U.S. Cl. ...................................... 378/040; 378/95
[58] Field of Search ................... 378/8, 40, 39, 97, 95

[56] References Cited

U.S. PATENT DOCUMENTS

| | | | |
|---|---|---|---|
| 3,737,660 | 6/1973 | Ando et al. | 378/39 |
| 3,908,126 | 9/1975 | Hudson et al. | 378/39 |
| 4,021,672 | 5/1977 | Franke | 378/39 |
| 4,039,837 | 8/1977 | Ohta et al. | 378/40 |
| 4,125,774 | 11/1978 | Ciavattoni et al. | 378/40 |
| 4,145,611 | 3/1979 | Välilä | 378/40 |
| 4,303,829 | 12/1981 | Wagner | 378/8 |

Primary Examiner—Alfred E. Smith
Assistant Examiner—T. N. Grigsby
Attorney, Agent, or Firm—Jack E. Haken

[57] ABSTRACT

A dental tomography apparatus comprises three drive motors for displacing the film and the X-ray source in two mutually perpendicular directions in a horizontal plane and for pivoting the carrier which connects the film and the X-ray source. The control signals for the motor drives are derived from the contour of the dentition by means of a plate which is covered by contacts on which the patient exerts a pressure by biting, so that the contacts whose position corresponds to the shape of the dentition are actuated. Therefrom, the contour of the dentition is determined by an arithmetic unit which supplies the control signals for the drive motors.

10 Claims, 14 Drawing Figures

DENTAL TOMOGRAPHY APPARATUS

This is a continuation of U.S. Pat. application Ser. No. 238,350, filed Feb. 26, 1981 and now abandoned.

The invention relates to a dental tomography apparatus, comprising a carrier which is pivotable about a vertical axis and on which there are mounted a radiation source and a film holder which is aligned with respect thereto, an adjusting device for the translatory displacement of the carrier in a horizontal plane, drive motors for the pivoting of the carrier, the translatory displacement of the carrier, and the displacement of a film within the film holder, and also comprising a digital control device for the control of the drive motors.

A dental tomography apparatus of this kind is known from German AS No. 26 30 135. The digital control device controls the two motors for the translatory displacement of the carrier in the horizontal plane so that the pivoting axis of the carrier follows a curve which at least substantially corresponds to the shape of the dentition. The drive motor for the carrier pivots the carrier so that the connecting line between the focal spot of the radiation source and a slit diaphragm of the film holder wherethrough the radiation is incident on the film extends approximately perpendicularly with respect to the curve. The film is transported within the film holder at a velocity which is proportional to and higher than the translation velocity of the carrier.

The sharpness of the panoramic radiograph made of the dentition curve by means of such an apparatus is dependent on the degree of correspondence between the curve along which the carrier is translated and the shape of the dentition. Therefore, the control device comprises several selectable control programs for each time an adjustment curve of the carrier. The selection can be realized, for example, by making a plaster cast of the dentition to be radiographed, said cast being compared with the various adjustment curves and the curve being selected which best corresponds to the shape of the dentition.

Even if a large number of control programs for a corresponding large number of different shapes of dentitions are stored, inaccuracies and hence unsharpness and distortion (because the magnification changes during the exposure) of the layer image may occur for various reasons. For example, an adjustment curve may be accidentally selected which corresponds only comparatively poorly to the shape of the dentition. It may also occur that the head of the patient is positioned during the exposure so that the symmetry plane of the dentition of the patient does not correspond to the symmetry plane or line of the preselected adjustment curve. It may also occur that the patient holds his head so that the tips of the teeth of the upper jaw are not situated in the horizontal plane traversed by the focal spot during tomography.

The present invention has for its object to construct a dental tomography apparatus of the described kind so that sharper, distortion-free layer images are obtained.

This object is achieved in accordance with the invention in that the digital control device comprises an element which is to be introduced into the mouth of the patient and which comprises pressure contacts which can be actuated by biting, and also comprises an arithmetic unit which calculates the control signals for the drive motors from the switching condition of the pressure contacts.

Thus, in order to make a layer image the element comprising pressure contacts is arranged in a given position within the mouth of the patient. The patient bites, so that the part of the pressure contacts which is situated between the tips of the teeth of the upper and the lower jaw is actuated. The switching condition of the individual pressure contacts (actuated and not actuated), therefore, characterizes the relevant shape and position of the dentition. This condition is interrogated by the arithmetic unit. After fixation of the head of the patient by head rests, the element may be replaced by a suitable bite block. From the switching condition, the arithmetic unit calculates the relevant dentition shape or a curve which very accurately approximates the shape of the dentition, and supplies corresponding control signals for the drive motors.

In a further embodiment in accordance with the invention, the element is formed by a plate provided with contacts which can be compressed by biting. Thus, the fact is taken into account that the tips of the teeth of a dentition generally are not situated exactly in one plane, thus causing problems in the case of pressure contacts which do not change their shape when actuated, because some contacts which are situated directly underneath or over a tooth tip would not be actuated. This risk is precluded in the case of compressible contacts, because all contacts situated between the teeth are actuated by biting, even if they are not simultaneously actuated.

A particularly suitable embodiment of the element in accordance with the invention consists of a base plate on which there are provided a plurality of studs of a material having a low modulus of elasticity, part of said studs having a height which is smaller than that of the other part, the inside which is remote from the base plate being provided with an electrically conductive coating, an elastic diaphragm being tensioned across the studs, said diaphragm being provided with a conductive layer on the side facing the studs. A material having a low modulus of elasticity is to be understood to mean herein a material which allows the studs to be compressed by a few millimeters with a comparatively low biting force, for example, sponge rubber or a similar material. During biting, first the diaphragm and the higher studs are compressed, until the conductive layer on the diaphragm contacts the conductive layer on the end face of the shorter studs which is each time connected to a signal lead. The diaphragm with the conductive layer and the end faces of the studs provided with an electrically conductive coating thus form pressure contacts, i.e. an electrical connection whose resistance can be varied by powers of ten in accordance with the pressure acting thereon. The higher studs which do not comprise an electrically conductive coating and at least four of which each time surround a stud provided with an electrically conductive coating ensure that the diaphragm cannot contact the studs comprising an electrical coating in the no-load condition.

The intensity of the radiation incident on the film is highly dependent on the relevant pivoting position of the carrier. For example, when the carrier is in a position in which a radiograph is made of the front teeth, the vertebral column will be irradiated at the same time, so that the radiation is substantially attenuated. Consequently, it may occur that this area on the film is exposed less than the other areas when the translatory movement in the horizontal plane is realized with a constant velocity in an absolute sense. Therefore, in a further embodiment in accordance with the invention there is provided a dose power measuring device whose output signal is applied to the arithmetic unit in order to control the speed of the drive motors in accordance with the dose power each time measured.

An embodiment in accordance with the invention will be described in detail hereinafter with reference to the accompanying diagrammatic drawing. Therein.

Figure 1:
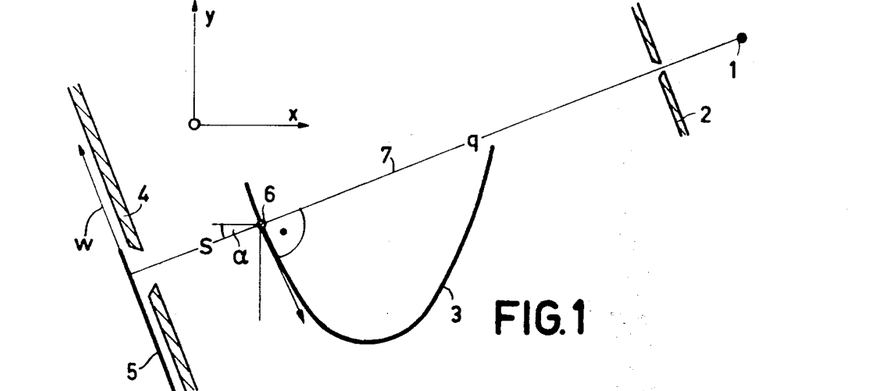
FIG. 1 shows the geometrical relationships in a dental tomography apparatus.

The reference numeral 1 in FIG. 1 denotes a radiation source, for example, an X-ray tube, whose radiation passes through a slit diaphragm 2 with a vertically situated slit, traverses the dentition whose shape is represented by a curve 3, and is incident, via a slit diaphragm 4 of a film holder (not shown) and whose slit also extends vertically, on a film 5 in the film holder. The radiation source 1 and the slit diaphragm 2 as well as the film holder (not shown) and the slit diaphragm 4 thereof are rigidly connected to a carrier whose direction is denoted by a line 7 and which can be pivoted about an axis 6. The distance between the axis 6 and the radiation source is denoted by the letter q and the distance from the film plane is denoted by the letter S. In order to make a layer image, the carrier must be moved in a horizontal plane so that its pivot axis 6 describes a path which coincides with the dentition curve 3. The carrier should at the same time be pivoted about the axis 6 so that the radiation traverses the dentition approximately perpendicularly. At the same time, the film 5 must be moved in the opposite direction at a speed which is proportional to the velocity of displacement of the pivoting axis 6, the proportionality factor corresponding to the magnification with which the dentition is imaged on the film. The magnification m is calculated in accordance with the equation:

$$m = (q+s)/s \tag{1}$$

For the speed w of the film 5 within the film holder, the following is then applicable:

$$w = m \cdot v \tag{2}$$

where v is the velocity at which the pivot axis 6 moves along the curve 3.

The value of the velocity v does not influence the sharpness of the layer image, but influences the exposure. This is because a uniformly exposed layer image of the dentition is obtained only if the velocity v is proportional to the dose power D(t) which may vary in accordance with the position of the carrier. For example, if the front teeth of the patient are to be irradiated, the vertebral column must be irradiated at the same time, so that the intensity is substantially reduced. Therefore, the displacement at the area of the front teeth must be slower. Therefore, for the velocity v:

$$v = c \cdot D(t) \tag{3}$$

in which c is a constant which depends on the geometry of the arrangement and on the sensitivity of the film. The instantaneous value of the dose power can be determined by means of a dose measuring device, for example, an ionization chamber, which is arranged in front of or behind the film. The shifting of the pivot axis in the plane of the drawing should in general be realized by means of two independent drive motors for the displacement in two mutually perpendicular directions, for example, in the y-direction and the x-direction shown in the drawing. The velocity components in these directions are then calculated in accordance with:

$$v = \sqrt{(dx/dt)^2 + (dy/dt)^2} = c \cdot D(t) \tag{4}$$

The velocity dy/dt of the drive in the y-direction then follows from the velocity dx/dt in accordance with the equation:

$$\frac{dy}{dt} = \frac{dy}{dx} \cdot \frac{dx}{dt} = y' \cdot \frac{dx}{dt} \tag{5}$$

in which y' is the first derivative of y according to x. From the equations (4) and (5) the following is obtained:

$$dx/dt = c \cdot D(t) / \sqrt{1 + (y')^2} \tag{6}$$

From the equations (5) and (6), the velocity in the y-direction is obtained:

$$dy/dt = y' \cdot c \cdot D(t) \sqrt{1 + (y')^2} \tag{7}$$

For the angle α to be enclosed by the carrier and the x-axis, the following is applicable:

$$\alpha = \text{arc } ctg(-y') \tag{8}$$

Figure 2A:
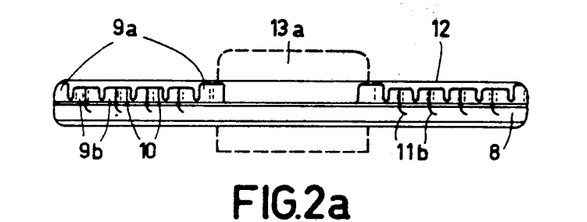
FIG. 2a is a side elevation of the element provided with pressure contacts.
Figure 2B:
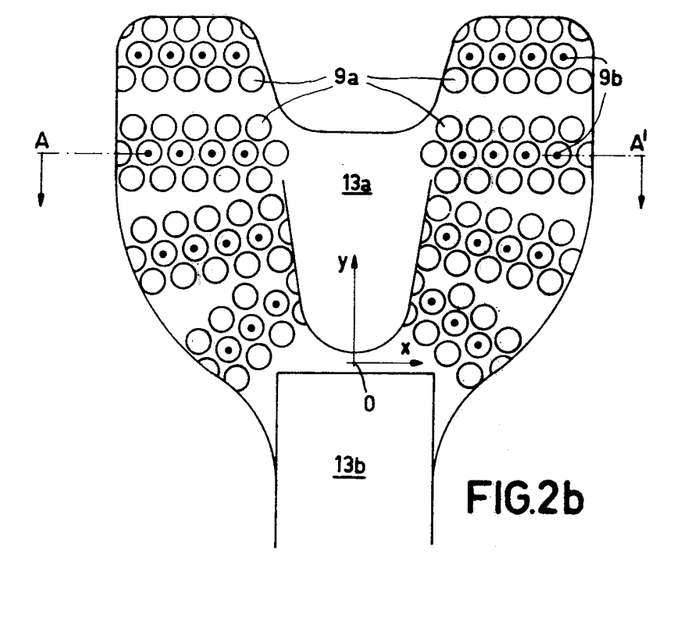
FIG. 2b is a plan view of the element.

The values α, dx/dt, dy/dt and w can be calculated only if y' is known. To this end, y must be known, i.e. an analytic function whose variation corresponds to the shape of the curve of the dentition. FIGS. 2a and 2b show an element for determining this function, FIG. 2a showing a cross-sectional view along the line a—a' in FIG. 2b, the element being shown at a scale of 2:1.

The element comprises a flat base plate 8 which is provided with a plurality of cylindrical studs of spunge rubber. There is a first group of slightly higher studs 9a and a second group of studs which are slightly lower, for example, ½ mm lower than the other studs and whose end face is provided with a conductive coating, each of which is connected to an electrical lead 11b which is passed through the interior of the plate or through the plate. Each of the lower studs 9b, provided with a dot in FIG. 2b and referred to hereinafter as switching studs, is surrounded by at least four higher studs 9a.

A rubber-like diaphragm 12 whose side facing the studs is provided with an electrically conductive layer is tensioned across the studs. In conjunction with the diaphragm 12, the switching studs 9b thus form switch or pressure contacts which are normally open and which are closed by a pressure exerted on the diaphragm over the relevant switching stud. As appears from FIG. 2b, a total of 30 switching studs are present, their position being given in the following table:

| x (cm) | y (cm) | x (cm) | y (cm) | x (cm) | y (cm) | x (cm) | y (cm) |
|---|---|---|---|---|---|---|---|
| +1.0 | 0.75 | +1.2 | 1.6 | +1.4 | 2.7 | +1.5 | 4.0 |
| −1.0 | 0.75 | −1.2 | 1.6 | −1.4 | 2.7 | −1.5 | 4.0 |
| +1.28 | 0.47 | +1.59 | 1.52 | +1.8 | 2.7 | +1.9 | 4.0 |
| −1.28 | 0.47 | −1.59 | 1.52 | −1.8 | 2.7 | −1.9 | 4.0 |
| +1.57 | 0.18 | +1.98 | 1.44 | +2.2 | 2.7 | +2.3 | 4.0 |
| −1.57 | 0.18 | −1.98 | 1.44 | −2.2 | 2.7 | −2.3 | 4.0 |
|  |  | +2.38 | 1.37 | +2.6 | 2.7 | +2.7 | 4.0 |
|  |  | −2.38 | 1.37 | −2.6 | 2.7 | −2.7 | 4.0 |

The position of the y-axis is given by the symmetry line of the body and the x-axis is situated as shown in FIG. 2b. In order to position the front teeth of the dentition in an at least approximately defined position with respect to the element, the base plate 8 is provided with raised portions 13a and 13b which project above the diaphragm 12, so that the incisors will be situated between the two raised portions (approximately in the coordinate origin).

During biting, at least one switching stud of every four or three switching studs each time juxtaposed in one line is actuated, but possibly also two or three. If only one switching stud is actuated, the coordinates of this switching stud are stored in the arithmetic unit, to be described with reference to FIG. 5, in order to characterize the dentition curve. When two switching studs are actuated, the mean value of their coordinates is formed, and when three switching studs are actuated, the coordinates of the central switching stud are stored for characterizing the position of the dentition curve. The switching condition of the switching studs, therefore, is characteristic of the shape of the dentition and its position with respect to the studded plate 8.

Figure 3:
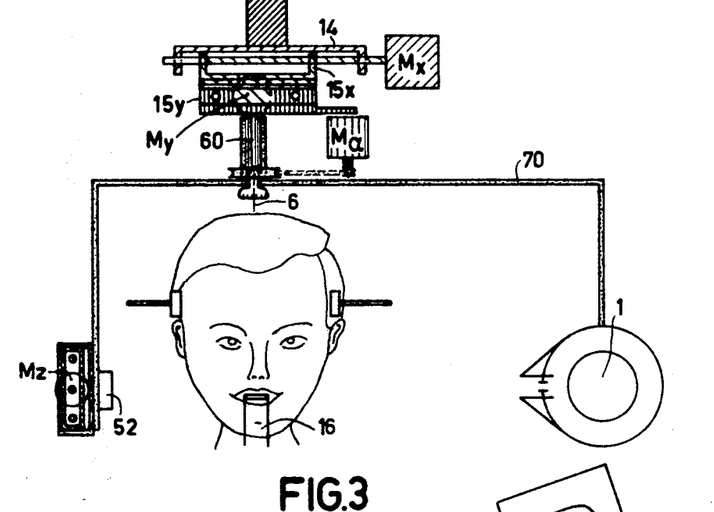
FIG. 3 is a side elevation of the apparatus.
Figure 4:
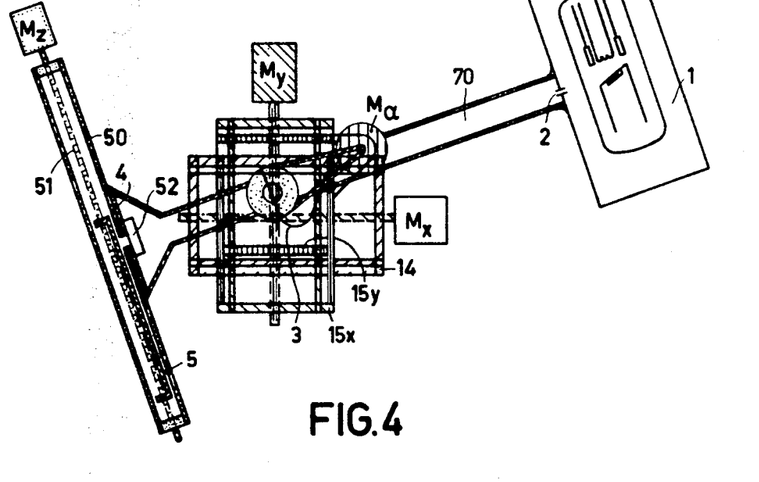
FIG. 4 is a plan view of the apparatus.

The mechanical construction of a dental tomography apparatus which is suitable for the application in accordance with the invention is shown in the FIGS. 3 and 4. On a stationary frame 14, being shaded from the bottom left to the top right in the drawing, there is mounted (in a manner not shown) a step motor $M_x$ which displaces the slide $15_x$ in the x-direction via a spindle drive. On the slide $15_x$ (shaded from the top left to the bottom right) there is provided a motor $M_y$ which is capable of displacing a further slide $15_y$ (vertically shaded) in the y-direction. The slide $15_y$ supports a vertical shaft 60, the central axis of which is identical to the axis 6 (see FIG. 1). A carrier 70 is pivotable about the shaft 60, one end of said carrier supporting the X-ray source 1 whilst its other end supports a film holder 50 which comprises the slit diaphragm 4 and in which the film 5 is arranged in a vertical plane which can be displaced perpendicularly to the horizontal plane by a further step motor $M_z$ and a spindle drive 51. The pivoting motion of the carrier 70 about the shaft 60 or the central axis 6 thereof is realized by means of a step motor $M \alpha$. Moreover, for the fixation of the head of the patient there are provided adjustable head rests 16. A bite block which can be introduced into the mouth of the patient at right angles to the beam path of the X-ray source and on which the patient bites for the purpose of fixation, ensures that the tips of the teeth are in a defined plane. A dose measuring device 52, which may also be arranged behind the film, supplies a signal which corresponds to the intensity of the X-rays behind the jaw of the patient.

Figure 5:
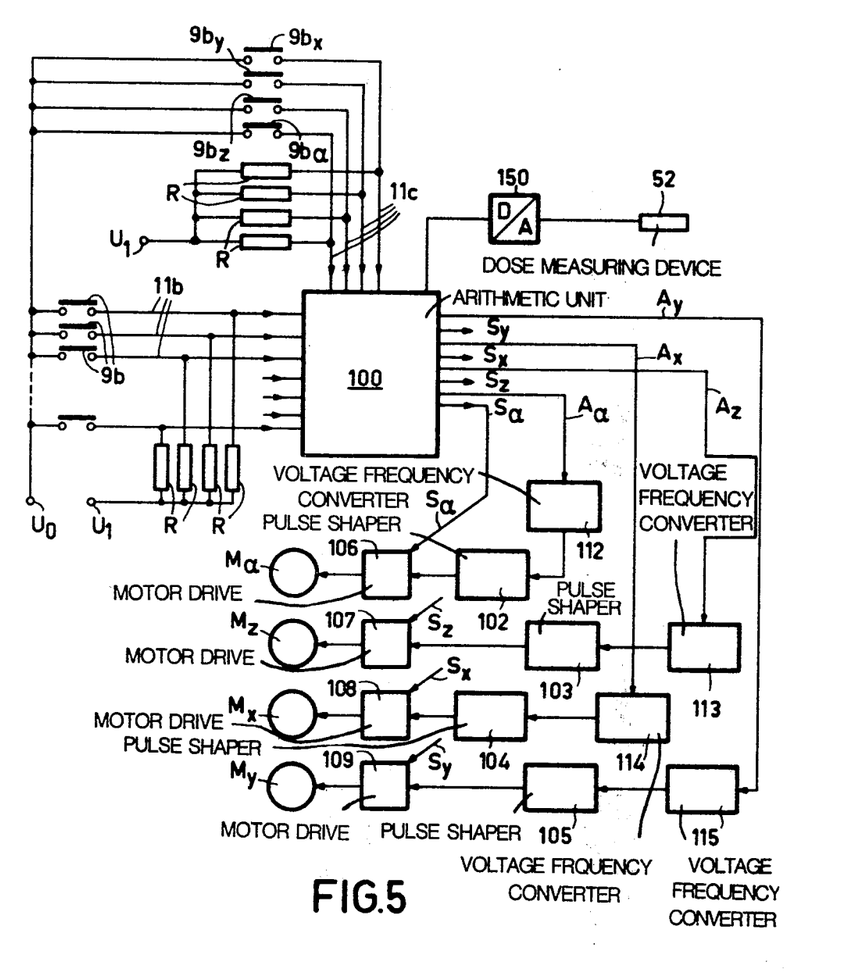
FIG. 5 shows a circuit for controlling the drive motors by means of a microcomputer

FIG. 5 shows the circuit arrangement for controlling the step motors. As has already been stated with reference to the FIGS. 2a and 2b, each of the switching studs 9b (FIG. 5 shows only four switching studs, even though a total of 30 studs are used) is connected to a lead 11b. The leads 11b are connected on the one side to the data inputs of an arithmetic unit 100 and on the other side, each time via a resistor R, to a potential $U_1$. The conductive lower side of the diaphragm 12 carries the potential $U_0$. Therefore, if the diaphragm is pressed down over a switching stud by the dentition, the associated lead 11b will carry the potential $U_0$; however, if the switching stud remains unactuated, the associated lead will carry the potential $U_1$. In the arithmetic unit, a binary signal 1 and 0 can be assigned to the two different potentials $U_1$, $U_0$, so that a bit sample corresponding to the shape of the dentition is formed.

The arithmetic unit 100 may be formed by a microcomputer consisting of a microprocessor and the necessary memories and input and output elements. Therein, inter alia the coordinates of the individual switching studs are stored. From the coordinates of the switching studs which are actuated by biting (whose associated line 11b thus carries the potential $U_0$), the arithmetic unit determines, in the manner to be described hereinafter, an analytic function $y=f(x)$, y preferably being a quartic polynomial, so that:

$$y = a_0 + a_1 x + a_2 x^2 + a_3 x^3 + a_4 x^4 \quad (9)$$

It has been found that it is efficient to store also the position of the incisors by three coordinate pairs (x, y): (-0.3;0), (0;0) and (0.3;0). The coefficients $a_0 \ldots a_4$ are then selected so that the sum of the squares of the distances between the coordinate pairs, determined by the switching studs and possibly calculated by determination of the mean value, on the one hand and the curve y on the other hand is minimized. The function y calculated by means of these coefficients generally corresponds very accurately to the actual shape of the dentition.

When the arithmetic unit 100 has determined the shape of the dentition, i.e. the coefficients $a_0 \ldots a_4$ of the function y, the derivative will also be directly available:

$$y' = a_1 + 2a_2 x + 3a_3 x^2 + 4a_4 x^3 \quad (10)$$

On the basis of the equation (10), the equation (8) can also be solved.

The output signal of the dose measuring device 52, corresponding to the dose D(t), is also applied, via an analog-to-digital converter 150, to the arithmetic unit, so that the latter determines all dentition-dependent parameters y, D(t) for the calculation of the velocities dx/dt, dy/dt, w and the relevant angular position α in accordance with the equations (6) to (8) and (2).

Each of the stepmotors $M_\alpha$, $M_z$, $M_x$ and $M_y$ is connected to an electronic motor drive circuit 106 ... 109, each of which receives a direction signal $S_\alpha$, $S_z$, $S_x$, $S_y$, respectively, on a first input, said direction signal determining the direction of rotation of the motors $M_\alpha$, $M_z$, $M_x$, $M_y$. On a second input, each of the motor drive circuits 106, ..., 109 receives a series of electrical pulses, the frequency of which determines the speed of rotation (step frequency) of the step motors $M_\alpha$, $M_z$, $M_x$, $M_y$. The series of electrical pulses are generated by pulse shaper stages 102 ... 105, the input of which is each time connected to an output of a voltage/frequency converter 112 ... 115, respectively. Each voltage/frequency converter 112 ... 115 produces a low-frequency signal which is dependent on the voltage level on the input of the converters 112 ... 115. The analog voltages on the inputs of the converters 112 ... 115 are supplied, together with the direction signals, by the arithmetic unit 100 as will be described in detail hereinafter.

The arithmetic unit first controls the motors $M_x$ and $M_y$ to a given initial position in which the film 5 is in a position z=0, the shaft 60 is in the position 0 (x=0 y=0) and the line 7 (FIG. 1) is directed transversely of the x-axis ($\alpha = \pi/2$). This initial position 0 (FIG. 2) is supervised by means of microswitches $9bx$, $9by$, $9bz$, $9b\alpha$ which are all closed as soon as the axis 6 (FIG. 1) reaches the coordinate origin 0 (FIG. 2) and the film 5 as well as the line 7, have reached their desired position. The microswitches $9bx$, $9by$, $9bz$, $9b\alpha$ (omitted in FIG. 3 for the sake of clarity) are mounted on the frame 14, the slide $15x$, the film holder 50 and the slide $15y$, respectively, and are actuated by the slide $15x$, the slide $15y$, the film 5 and the shaft 60, respectively, as soon as these elements have reached the desired position (x=0, y=0, z=0, $\alpha = \pi/2$). From the initial position 0, the dental tomography apparatus is moved to a starting position along the curve determined by means of the arithmetic unit 100. The starting position is situated at an end point of this curve, for example, ("top left") on the curve according to the equation (9) it is situated at x<0, so that $y_M = 4.5$ cm. Moreover, the arithmetic unit controls the step motor M $\alpha$ for the pivoting of the carrier in accordance with the equation (8) so that the carrier moves transversely of the curve y, and it controls the step motor $M_z$ so that the film cassette reaches a starting position. The arithmetic unit 100 then calculates, each time for a time increment $\Delta t$ (for example, 50 ms), how many steps the four step motors have to perform within this time increment. In general, for the $n^{th}$ time increment:

$$\Delta x_n = \frac{c \cdot D_{n-1}}{\sqrt{1 + (y'_{n-1})^2}} \cdot \Delta t = x_n - x_{n-1} \quad (11)$$

Therein, $D_{n-1}$ is the dose or the mean value of the dose power during the preceding time increment; $y'_{n-1}$ is calculated for $x = x_{n-1}$ in accordance with the equation (10); $\Delta x_n$ is the distance over which the carrier or its pivot axis must be shifted in the x direction; it is proportional to the number of steps. Therefrom, it is possible to determine the frequency $F_{xn}$ which has to be produced by the converter 114 in order to ensure that the motor $M_x$ displaces the slide $15_x$ exactly over the distance $\Delta x_n$ during the $n^{th}$ time increment $\Delta t$:

$$F_{xn} \approx \frac{\Delta x_n}{S_x \cdot \Delta t} = \frac{V_x \cdot \Delta t}{S_x \cdot \Delta t} = \frac{dx}{dt} \cdot \frac{1}{S_x} \quad (12)$$

Therein, $F_{xn}$ is the frequency to be generated and $s_x$ is the distance over which the step motor $M_x$ displaces the slide $15_x$ during one step.

For the other step motors:

$$\Delta y_n = y_n - y_{n-1} \quad (13)$$

$y_n$ is calculated in accordance with equation (9) for the value $x_n$ determined in accordance with the equation (11). $y_{n-1}$ has already been calculated during the previous time increment. The pivoting movement $\Delta \alpha_n$ during the $n^{th}$ time increment is calculated as follows:

$$\Delta \alpha_n = \text{arc } ctg(=y'_n) - \alpha_n \quad (14)$$

$$\omega_n = \Delta \alpha_n / \Delta t \quad (14b)$$

$\alpha_n$ is still known from the previous time increment. The displacement $\Delta z_n$ is calculated as follows:

$$\Delta z_n = m \cdot \sqrt{(\Delta x_n)^2 + (\Delta y_n)^2} \quad (15)$$

The variables $\Delta y_n$, $\Delta \alpha_n$ and $\Delta z_n$ can be assigned, analogous to the equation (12) a frequency $F\alpha$, $Fz$ and $Fy$ which is supplied, by way of a proportional voltage value $W_\omega$, $Vz$, $Vy$, from the arithmetic unit output to the voltage frequency converters 112 ... 115. For the first time increment, an estimated value $D_0$ must be used in the equation (11).

Under the control of the arithmetic unit, the velocity in the x, the y and the z direction as well as the angular velocity of the pivoting movement will be constant each time during the time increment $\Delta t$ and each of the step motors will generally perform a large number of steps (for example, more than 20) during such a time increment. This means that the calculated curve is approximated by a large number of straight lines (from 200 to 400). (The overall duration of an exposure is from 10 to 20 seconds). In reality, the velocity, however, should continuously change, at least from step to step. Therefore, the arithmetic unit can also be programmed so that for each step motor it calculates the period of time which must expire until the next step (in the case of a constant step value), and that at the calculated instant it supplies a control pulse directly to the pulse shapers 106 ... 109 preceding the relevant step motors $M\alpha ... M_y$. In that case the velocity may also change from step to step, so that the accuracy is even further improved.

Figure 6:
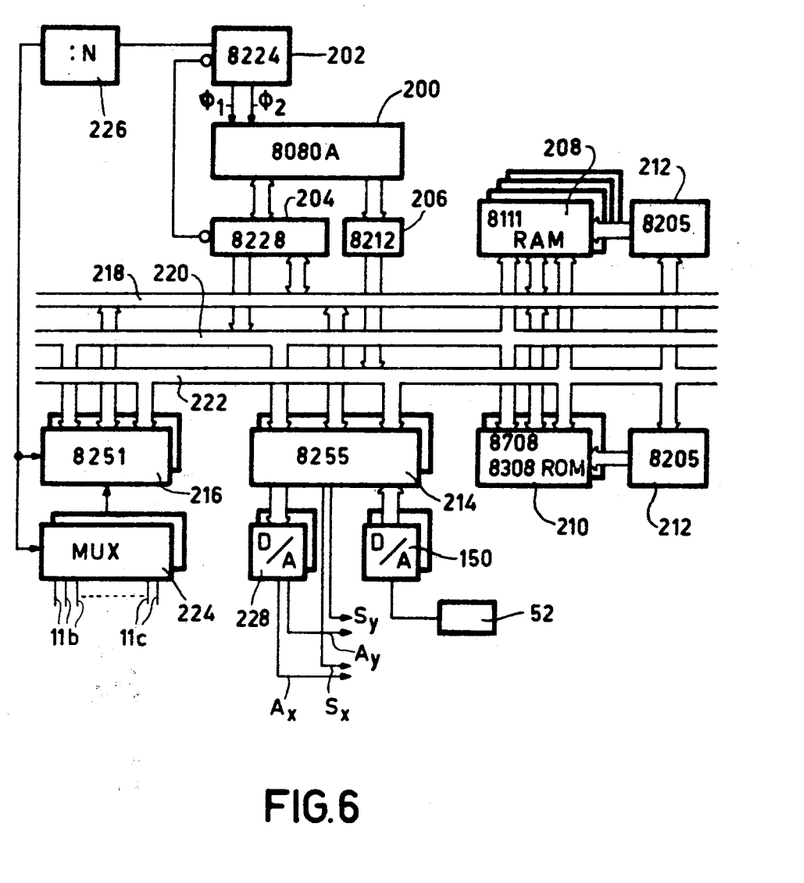
FIG. 6 shows an embodiment of the microcomputer.

FIG. 6 is a detailed representation of the arithmetic unit 100 shown in FIG. 5. The arithmetic unit 100 comprises a microprocessor 200 (Intel 8080A), a clock generator driver 202 (Intel type 8224), a bidirectional bus driver 204 (type 8228), an address buffer 206 (type 8212), a random access memory 208 (type 8111), a read-only-memory 210 (type 8308 or 8708), an address decoder 212 (type 8205) and input and output interfaces 214 and 216 (type 8255 and 8251) which are interconnected by means of a data bus 218, a control bus 220 and an address bus 222. The control and data outputs of the microprocessor 200 are connected to the control bus (220) or the data bus (218) via the bus driver circuit 204. The address outputs of the microprocessor 200 are connected to the inputs of the address buffer 206, the outputs of which are connected to the address bus 222.

Each of the memories 208 and 210 operates with an address decoder 212 to ensure that the microprocessor 200 has sufficient storage capacity available. The input terminals (A0, A1, A2, $\overline{E1}$, $\overline{E2}$) of the address decoder 212 are connected to a part (A10-A15) of the address bus (A0 ... A15). The outputs of the address decoder 212 select a part of the total storage space (by means of the CS inputs of the integrated memory circuits) wherefrom a storage location becomes accessible with the remaining part of the address bus (A0-A9). In the random access memory 208, the available or calculated data variables are stored. In the read-only memory 210, the individual instructions or sequences are stored, such as the coefficients $a_1 \ldots a_4$ of the various curves.

The input and output interfaces comprise a circuit 214 for receiving serial data and a circuit 216 for input and output of parallel data. Using the circuit 214 and a synchronized multiplex circuit 224 (both circuits receive synchronization signals derived, by means of a frequency divider 226, from the oscillator frequency of the clock generator 202), the information on the lines 11b or 11c is serially read and temporarily stored. Subsequently, the data is transported in parallel on the data bus 218, followed by further processing. After determination of the data for the control of the motors $M_x$, $M_y$, $M_z$, $M_\alpha$ by the microprocessor 200, this data is output in parallel via the input and output circuit 214. The outputs of the circuit 214 are group-wise applied to each time a digital-to-analog converter 228, the output signal $A_x$, $A_y$, $A_z$, $A_\alpha$ of each converter 228 being proportional to the desired velocity $V_x$, $V_y$, $V_z$, $\omega_\alpha$. Each output signal $A_x$, etc. is associated with a direction signal $S_x$, $S_y$, $S_z$, $S_\alpha$ which determines the direction of rotation (clockwise or counter-clockwise) of the motors $M_x$, $M_y$, $M_z$, $\alpha$. The direction signal is applied without conversion from the output circuit 214 to one of the motor drive circuits 106 ... 109. Furthermore, the input and output circuit 214 transports the dose power D(t), measured by the dose power measuring device 52 and digitized by the analog-to-digital converter 150, on the data bus in parallel bit format for further processing by the microprocessor 200.

Figure 7:
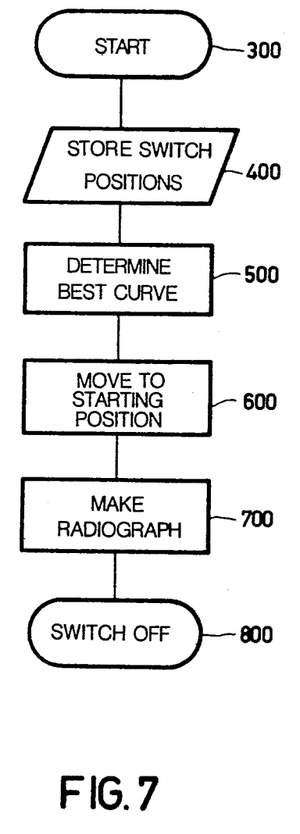
FIGS. 7 to 11 show flow charts of the control of the dental tomography apparatus in accordance with the invention.

FIG. 7 shows a basic diagram for the execution of the program of the arithmetic unit 100. After the starting of the program (300), the switching condition of the switches 11 on the base plate 8 is read and stored during a first part of the program (400). Using the stored switching conditions during a second part of the program (500) a curve is determined which best approximates the actual dentition curve. During a third part of the program (600), the dental tomography apparatus is moved to a starting position which is determined by the dentition curve determined. During the part of the program (700), the radiograph of the dentition is made, the apparatus being controlled by the arithmetic unit 100 by way of the calculated data. After the exposure, the apparatus is switched off (800).

Figure 8A:
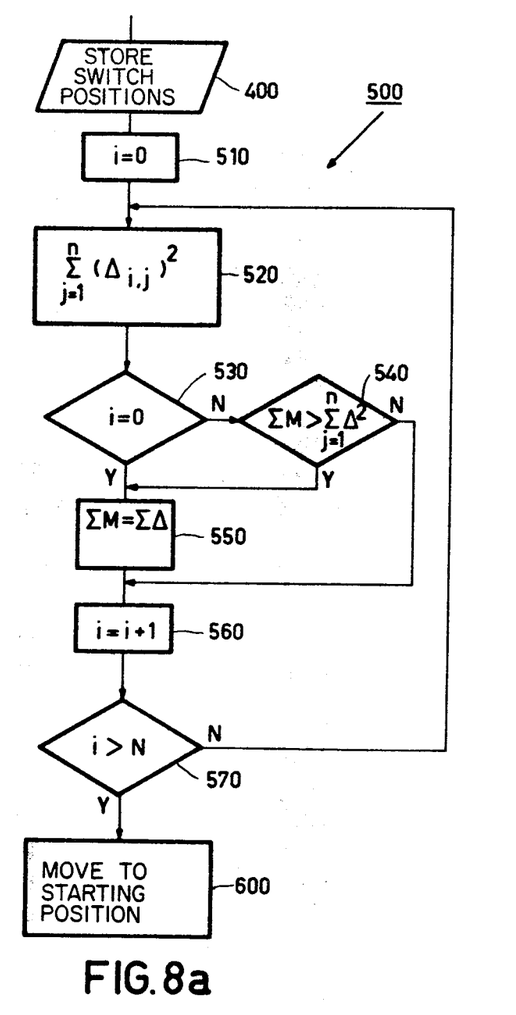

FIG. 8a shows a detail of the flow-chart for determining a curve which approximates the actual dentition curve. It is assumed that a plurality of N (for example, N=64) different curves are stored in the memory 210, which means that for each curve the coefficients $a_{1,i} \ldots a_{4,i}$ are stored ($0 \leq i \leq 64$). Furthermore, for each curve the x-values and y-values are stored for which the y-values correspond to the y-values of the switches 9b on the base plate 8. After it has been tested (400) for each switch 9b whether or not it is in the closed condition, the switch condition being stored, the coordinate values of the closed switches 9b are compared with the coordinates on a first curve (i=0, step 510–520) which have the same coordinate values for the y-values.

The difference $\Delta_{o,j}$ is then formed, that is to say the distance in the x-direction between the two points ($x_j$, $y_j$) of the switch and the intersection (x, $y_j$) of the curve i with the coordinate line $y=y_j$. This is more clearly shown in FIG. 8b. In the x-y coordinate system, the coordinates ($x_1$, $y_1$) ... ($x_4$, $y_4$) of four closed switches are shown. Two curves (i=0, i=m) are also shown in the coordinate system. The distance between the coordinate point ($x_j$, $y_j$) associated with a switch j and the intersection of the curve i=0 with the line $y=y_j$, is denoted by the reference $\Delta_{i,0}$. The distance between the point ($x_2$, $y_2$) and the intersection of the curve i=0 with the line $y=y_2$ is denoted by the reference $\Delta$ 0,2, etc.

FIG. 8a shows that during the program step 520 first the sum $$\sum_{j=1}^{n} (\Delta_{0,j})^2$$

is calculated for the curve i=0, n being the number of closed switches. It is to be noted that the distances between switch coordinates and intersections must be calculated to the left (x<0) as well as to the right (x=0) of the y-axis. The x-value (positive or negative) is then used for the comparison of the associated intersections and switch coordinate values in order to form the difference. The calculated sum $\Sigma\Delta^2$ will have a minimum value if the curve approaches all switches 9b as well as possible. When the sum $\Sigma\Delta^2$ is calculated for the first time (i=0, test step 530), a test number $\Sigma M$ is made equal to $\Sigma\Delta^2$ (the minimum thus far) and the variable "INDEX" is made equal to i (step 540). The variable "INDEX" indicates which set of coefficients $a_{i,1} \ldots a_{i,4}$ is associated with the curve whose associated sum $\Sigma\Delta^2$ is minimum. The numerator i is incremented by 1 (setp 560) and subsequently it is tested whether i is larger than N, N being the number of curves stored. Because i=1, the program continues with the step 520, $\Sigma\Delta^2$ then being calculated for the curve having the coefficients $a_{1,1} \ldots a_{1,4}$. Because i≠0, it is then tested whether the newly calculated value $\Sigma\Delta^2$ is smaller than the test number $\Sigma M$. If not, the test number $\Sigma M$ and the variable INDEX are not changed (no better approximation determined) and the program continues with step 560. If $\Sigma\Delta^2$ is smaller than $\Sigma M$, a better approximation has been found than the one determined thus far, and the test number $\Sigma M$ becomes $\Sigma\Delta^2$ and the variable INDEX becomes i (program step 550).

This program part 500 (steps 510–570) is completed N times, the test number $\Sigma M$ and the variable "INDEX" being adapted as soon as the value $\Sigma\Delta^2$ becomes smaller than the test number for a curve. As a result, after the completion of the program part 500, the variable INDEX will indicate the set of coefficients $a_{1,1} \ldots a_{1,4}$ associated with the curve which best approximates the actual dentition curve.

Figure 9A:
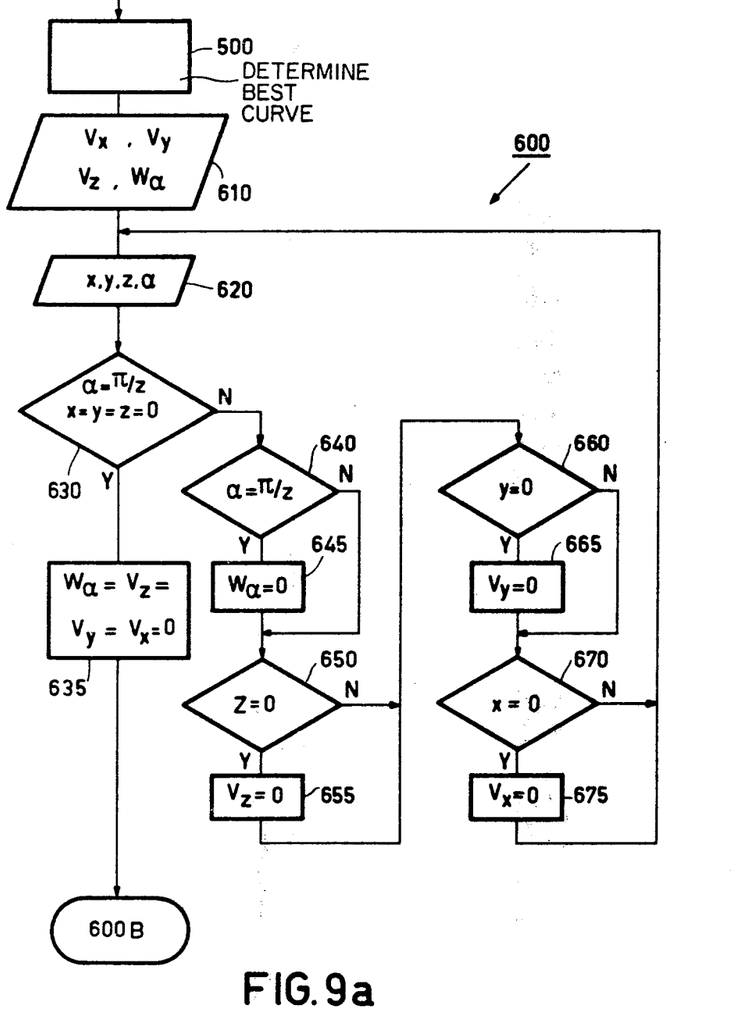

As has already been stated, before the start of the exposure, the parts of the apparatus which are driven by the motors Mx, My, Mz and $M\alpha$ are first placed in an initial position (x=0, y=0, z=0,$\alpha=\pi/2$), after which the motors move said parts to a starting position in which the exposure is started. The moving of the parts to the initial position in necessary because the apparatus is still in a final position after the previous exposure. During the next program step (610) of the program part (600) (FIG. 9a), therefore, the control signals $V_x$, $V_y$, $V_z$ and $W_{60}$ are supplied for the control of the motors $M_x$, $M_y$, $M_z$, $M_\alpha$. During the next step (620), the positions x, y, z and $\alpha$ are read by way of the microswitches 9bx, 9by, 9bz, 9b$\alpha$, (FIGS. 5 and 6). If the conditions $x=y=z=0 \Delta\alpha=\pi/2$ are satisfied (initial position reached, all microswitches closed), the control signals are all set to zero (635). Subsequently, the dental tomography apparatus is moved to its starting position, in accordance with the program part (600 B). If the conditions (step 630) are not satisfied, it is tested whether the individual coordinates ($\alpha=\pi/2$, $z=0$, $y=0$, $x=0$) have been reached (steps 640, 650, 660, 670). If one or more conditions have been satisfied, the associated signal ($W_\alpha$, $V_z$, $V_y$, $V_x$) is set to zero (steps 645, 655, 665, 675). Subsequently, the newly reached coordinates are read (620), after which they are tested, etc. The loop (620), 630, 640–675) is completed again until the conditions of step (630) have been satisfied.

The tomography apparatus is subsequently moved from the initial position to the starting position, the arithmetic unit 100 then controlling the motors $M_x$, $M_y$, $M_z$, M on the basis of the program part shown in FIG. 9b so that the starting position along the curve determined is reached. During the step 680, first the variables "SIGN" and D are made equal to $-1$ and Do, respectively (Do could correspond to approximately the mean dose power). The variable SIGN determines the direction of rotation of the various motors $M_x$, $M_y$, $M_\alpha$ and $M_z$. The variable D determines the speed of rotation of these motors and has a fixed value for as long as no dose power of the X-ray tube 1 is measured. During the subsequent step 685, the initial values are calculated for the control of the motors $M_x$, $M_y$, $M_z$, $M_\alpha$ in accordance with the formulas (6), (4) and (2), respectively; in this respect it is to be noted that for the initial position y' as well as $dy/dt=V_y$, $d\alpha/dt=W\alpha$ are zero. Subsequently, the newly reached coordinates $x_n$, $y_n$, $z_n$ and $\alpha$ n are calculated (960). After calculation of the initial values of the control, a sub-routine 900 is addressed for further control of the apparatus. The sub-routine will be described in detail hereinafter with reference to FIG. 11. After completion of the sub-routine 900, it is tested whether the maximum value $y_M$ has been reached. If this is not the case, the sub-routine 900 is addressed again, etc. If the maximum value $y_M$ has been reached, the program part 700 which controls the tomography apparatus during an exposure may commence.

Figure 8B:
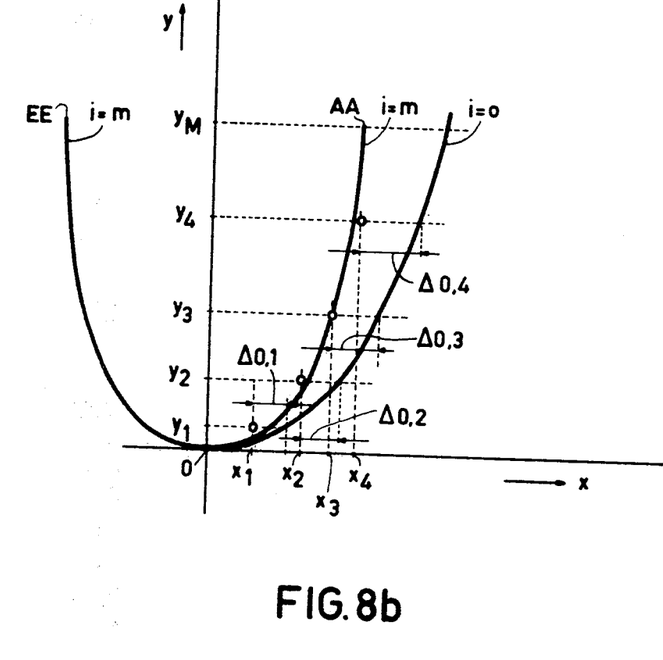
Figures 9B, 10:
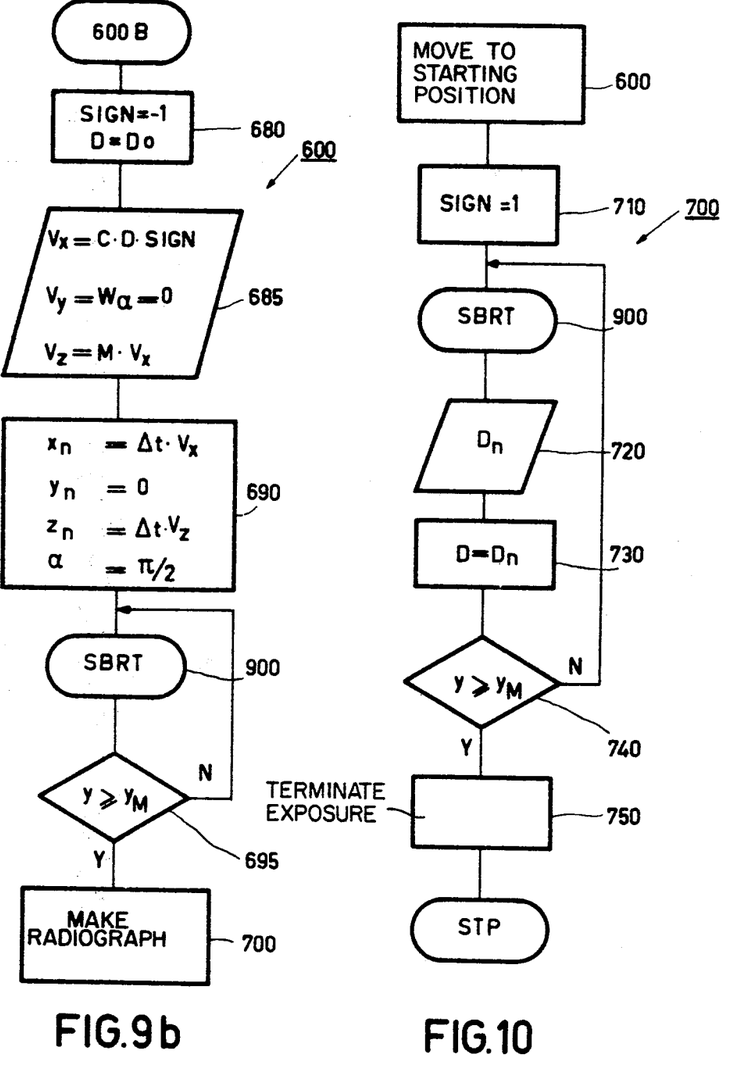

The program part 700 is shown in detail in FIG. 10. During the first step 710, the exposure is started and the variable SIGN obtains the value $+1$ in order to ensure that the control signals $V_x$, $V_y$, $V_z$, $W_\alpha$ control the motors $M_x$, $M_y$, $M_z$, $M_\alpha$ in the opposite direction with respect to the program part 600. Subsequently, the sub-routine 900 is addressed which determines the control signals $V_x$, $V_y$, $V_z$ and $W_\alpha$ as well as the new coordinates. During the next step 720, the dose rate supplied by the X-ray tube is read by the arithmetic unit 100 in order to ensure that the dose rate is taken into account for the calculations required for the next control signals in the sub-routine 900. During the step 730, the variable D (having a fixed value until then) obtains the measured dose power value $D_n$. During the step 740, it is tested whether the maximum value $y_M$ has been reached. (During the program part 600, the axis 6, 60, (FIGS. 1,3) has been moved to the point AA (FIG. 8b). Because the variable SIGN is converted from negative into positive, the axis 6,60 is first moved away from the value $y_M$ (point AA), and the y-value increases again only after the passage of the point (0)). As soon as this value $y_M$ has been reached, the exposure curve has been completely tracked, and the exposure may be terminated (750). This completes the program part 700.

However, if the values $y_M$ has not been reached, the sub-routine 900 is addressed again. The sub-routined 900 calculates, on the basis of the previously determined coordinates $x_n$, $y_n$, $z_n$ and $\alpha_n$ and the newly measured dose power Dn, the new control signals $v_x$, $v_y$, $v_z$ and $W_\alpha$ as well as the new associated coordinates $x_n$, $y_n$, $z_n$, $\alpha_n$. The loop 900-720-730-740 is completed until the condition (step 740) has been satisfied and the exposure may be terminated.

Figure 11:
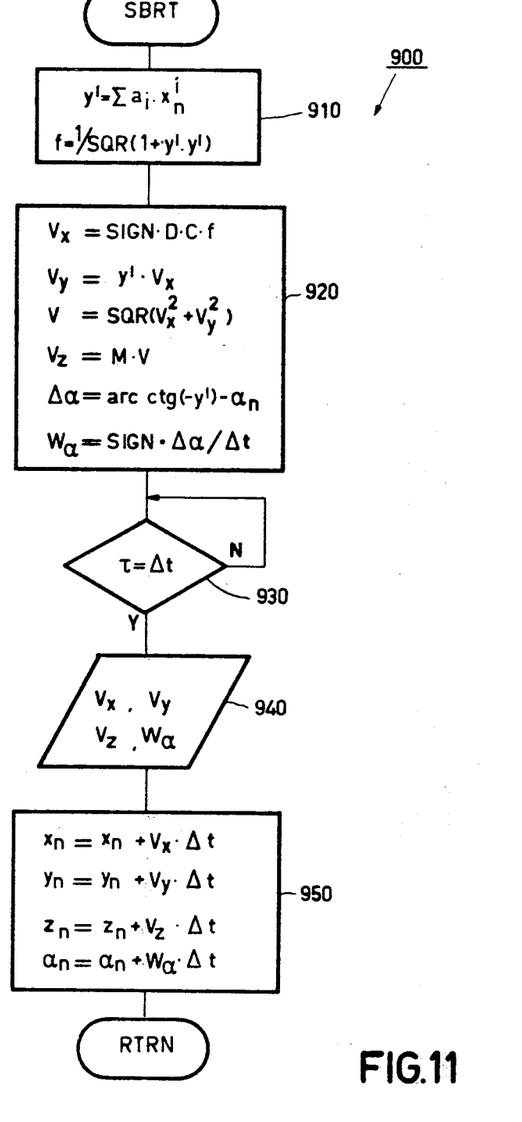

The sub-routine 900 is shown in FIG. 11. During the first step (910) of the sub-routine 900, the value y' (dependent on the relevant value of $x_n$) is calculated as well as the value $f=1/\sqrt{1+y' \cdot y'}$. During the second step (920), the control signals $v_x$, $v_y$, $v_z$ and $w_\alpha$ are calculated by means of the formulas (6), (5), (4) and (2), as well as (14) and (14b). The step includes a waiting loop. For as long as the time increment $\Delta t$ has not yet expired, no new control signals $v_x$, $v_y$, $v_z$, $W_\alpha$ may be applied to the step motors $M_x$, $M_y$, $M_\alpha$, $M_z$ or to their control circuits 102 ... 109. The variable $\tau$ is a counter content which contains the number of pulses generated by the clock generator driver 202 after the beginning of the time increment $\Delta t$. As soon as $\tau$ reaches a value which corresponds to the expiration of the time increment $\Delta t$, the next program step (940) will be executed; the newly determined control signals $V_x$, $V_y$, $V_z$, $W_\alpha$ are then applied to the control circuits 102 ... 115. After the control signals have been applied to the control circuits 102–115, the new coordinates $x_n$, $y_n$, $z_n$ and $\alpha_n$ are calculated; the previously determined control signals $V_x$, $V_y$, $V_z$, $W_\alpha$ are then taken also into account ($x_n=x_n+v_x\cdot\Delta t$, etc., program step 950). This completes the sub-routine 900, after which the program returns to the program part 600 or 700, depending on the point where the program has been interrupted for the execution of the sub-routine steps.

What is claimed is:

1. Apparatus for dental tomography comprising:
an array of electrical contacts which are activated by biting and are adapted for insertion into the mouth of a patient;
an X-ray source;
a film holder; and
means for moving the source and film holder around the head of the patient along a path which is determined by a pattern of activated contacts in the array.

2. A method of dental tomography comprising the steps of:
inserting an array of electrical contacts, which are activated by the pressure of biting, into the mouth of a patient;
determining the shape of the patient's dentation on the basis of signals provided by the activation of the contacts; and
displacing an X-ray source and radiographic film about the head of the patient in a path which corresponds to the determined shape of the detentation to produce a tomographic image of the dentation on the film.

3. In dental tomography apparatus comprising:
a carrier which is pivotable about a vertical axis;
a radiation source mounted on the carrier;
a film holder mounted on the carrier and aligned thereon with respect to the radiation source;
adjusting means for translatory displacement of the carrier in a horizontal plane;
drive motor means for pivoting the carrier, for translatory displacement of the carrier, and for displacement of a film within the film holder; and
means for controlling the drive motor means;

the improvement wherein the means for controlling comprises a switching element, adapted for introduction into the mouth of the patient, which includes pressure contact means for actuation by biting and the means for controlling further comprise an arithmetic unit which calculates, on the basis of the switching condition of the pressure contacts, control signals for operating the drive motor means.

4. Apparatus as claimed in claim 3 wherein the switching element comprises a plate and contacts which can be compressed by biting disposed on the plate.

5. Apparatus as claimed in claims 3 or 4 wherein:
the plate includes a plurality of projecting studs of an elastic material having a low modulus of elasticity, a first group of the studs having a height which is smaller than that of the remaining studs;
the contacts comprise an electrically conductive coating disposed on a side of said studs which is remote from the plate, an elastic diaphragm tensioned across said studs adjacent said electrically conductive coating and an electrically conductive layer disposed on said diaphragm adjacent the electrically conductive coating on said studs.

6. Apparatus as claimed in claims 3 or 4 further comprising dose power measuring means which are connected to the arithmetic unit to control the speed of the drive motor means as a function of a measured dose power.

7. Apparatus as claimed in claims 3 or 4 wherein the arithmetic unit comprises a memory for storing coordinates of the contacts and data representing several different curves and further comprises comparison means for comparing the coordinates of closed contacts with a first portion of the data representing the curves and for determining, for each curve, a numerical value which is a measure of the differences between the coordinates of the closed contacts and the first part of said data, wherein said arithmetic unit calculates control signals for the drive motor means from a second part of the data which is associated with the curve for which said determined numerical value is smallest.

8. The apparatus of claim 7 wherein the first part of the data stored in memory defines coordinates of different points on each curve, a coordinate of each point corresponding to the coordinate of one of the contacts.

9. Apparatus as claimed in claim 7 wherein each curve is a high degree polynomial and the second part of the data stored in the memory are sets of coefficients associated with the polynomials.

10. The apparatus of claim 9 wherein the polynomials are forth degree polynomials.

* * * * *